United States Patent [19]
Hochmeister et al.

[11] Patent Number: 6,085,907
[45] Date of Patent: Jul. 11, 2000

[54] FOLDABLE CARDBOARD BOX FOR CONTACT-FREE DRYING AND LONG-TERM STORAGE OF BIOLOGICAL EVIDENCE RECOVERED ON COTTON SWABS AND FORENSIC EVIDENCE COLLECTION KIT INCLUDING SAME

[75] Inventors: Manfred N. Hochmeister, Bern, Switzerland; Henry C. Lee, Branford, Conn.

[73] Assignee: Institute of Legal Medicine, University of Bern, Bern, Switzerland

[21] Appl. No.: 09/075,518

[22] Filed: May 11, 1998

[51] Int. Cl.[7] ................................................. B65D 69/00
[52] U.S. Cl. ...................... 206/569; 206/362.4; 206/570; 206/459.5; 206/486; 206/784
[58] Field of Search .................................... 206/456, 569, 206/362.4, 361, 362, 570, 459.5, 486, 418, 438, 784; 229/152, 102, 118

[56] References Cited

U.S. PATENT DOCUMENTS

| 1,039,026 | 9/1912 | Carter | 206/418 |
|---|---|---|---|
| 1,726,732 | 9/1929 | Doran | 206/486 |
| 2,950,040 | 8/1960 | Bolding | 229/118 |
| 3,182,885 | 5/1965 | Maio | 206/418 |
| 3,214,075 | 10/1965 | Champlin et al. | 229/152 |
| 3,246,740 | 4/1966 | Guyer | 206/362 |
| 4,873,193 | 10/1989 | Jensen et al. | 206/459.5 |
| 4,890,789 | 1/1990 | Lo Duca | 229/153 |
| 5,207,374 | 5/1993 | Lo Duca | 229/102 |
| 5,353,803 | 10/1994 | Corra | 128/749 |
| 5,402,889 | 4/1995 | Hermann et al. | 206/443 |
| 5,477,863 | 12/1995 | Grant | 128/749 |
| 5,494,166 | 2/1996 | Kuwata et al. | 206/528 |

*Primary Examiner*—Paul T. Sewell
*Assistant Examiner*—Nhan T. Lam
*Attorney, Agent, or Firm*—Irah H. Donner; Suresh Koshy; Pepper Hamilton LLP

[57] ABSTRACT

A biological evidence collection apparatus provides contact-free drying, storage, identification, and protection against sample switch and contamination of collected biological samples. The apparatus may include the described forensic evidence collection kit which provides a set of tools for the collection and storage of biological evidence. The collection apparatus may also be used as part of a sexual assault evidence collection kit, or a kit for the collection of buccal swabs, and the like.

6 Claims, 13 Drawing Sheets

FIG. 1

PRIOR ART

FOLDABLE CARDBOARD BOX FOR CONTACT-FREE DRYING AND LONG-TERM STORAGE OF BIOLOGICAL EVIDENCE RECOVERED ON COTTON SWABS AND FORENSIC EVIDENCE COLLECTION KIT INCLUDING SAME

BACKGROUND OF THE INVENTION

1. Field of the Invention

This invention relates generally to evidence collection kits, and components therefor. More specifically, this invention relates to a biological evidence collection apparatus which may be used to provide contact-free drying, long-term storage, protection against sample switch and contamination, and identification of collected biological samples. The apparatus may be included in a kit which provides a set of tools for the collection and storage of biological evidence or other evidence.

2. Background of the Related Art

The analysis of biological evidence has become an important tool for state and federal investigators who are attempting to identify a person who has committed a violent crime. Samples of blood, semen, and other body fluids can often provide investigators with substantial information about the perpetrator. For example, if a blood sample taken from a crime scene precisely matches that of a particular suspect, the match can be used to directly link the suspect to the scene of the crime. Such evidence can also be valuable in civil investigations such as paternity suits.

Investigators may collect body fluid evidence from a crime scene by wiping it onto a cotton-tipped swab or a cotton pad. A prior method of collecting biological evidence is the placement of such evidence-containing swabs or pads into a paper or plastic container or bag, known as an evidence container or bag, for future storage and handling. The evidence bag may be sealed, and the investigator may write on the bag or place a label on the bag to provide some identification of the evidence.

However, several problems exist with such a collection system. First, each bag can store only one sample, as a bag provides no means to prevent multiple samples from coming into contact with each other. Second, a swab or pad may become contaminated, or the amount of evidence on the swab or pad may be diminished, when a wet swab or pad is placed into the bag because the swab or pad must contact the inside of the bag.

Figure 1:
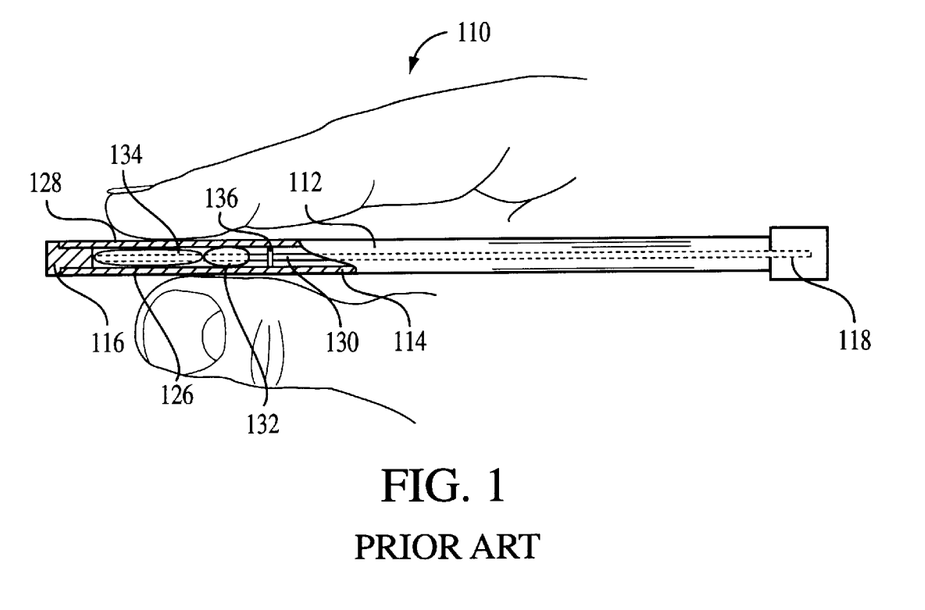
FIGS. 1–4 depict prior art examples of evidence collection and/or preservation devices.

Prior attempts to facilitate the collection of biological material include U.S. Pat. No. 4,211,323, issued to Olsen, incorporated herein by reference, which relates to a disposable diagnostic swab assembly as illustrated in FIG. 1. This assembly includes an elongated tubular plastic member 112, a cotton-tipped swab 132, and a plastic cap which is integral to the swab and which fits over the tubular member. The tubular member includes a pouch 178 which holds a culture medium 126 to provide an environment in which a biological sample can live.

The user collects a sample on the cotton-tipped swab and then places the swab into the tubular member such that the pouch is broken and the culture medium is released. The user then places the cap on the tubular member for the storage of the swab. The device in Olsen contains several disadvantages for forensic evidence. First, the device only allows for the storage of a single cotton-tipped swab. In addition, the device in Olsen contains solution and does not allow for contact-free drying. Further, this device provides no means for identification, labeling, or sealing to prevent tampering or contamination.

Figure 2A:
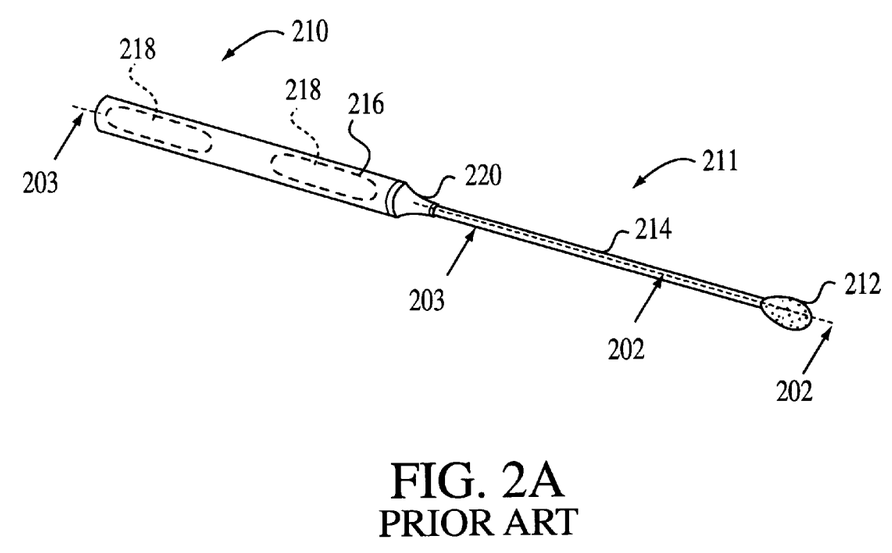
Figure 2B:
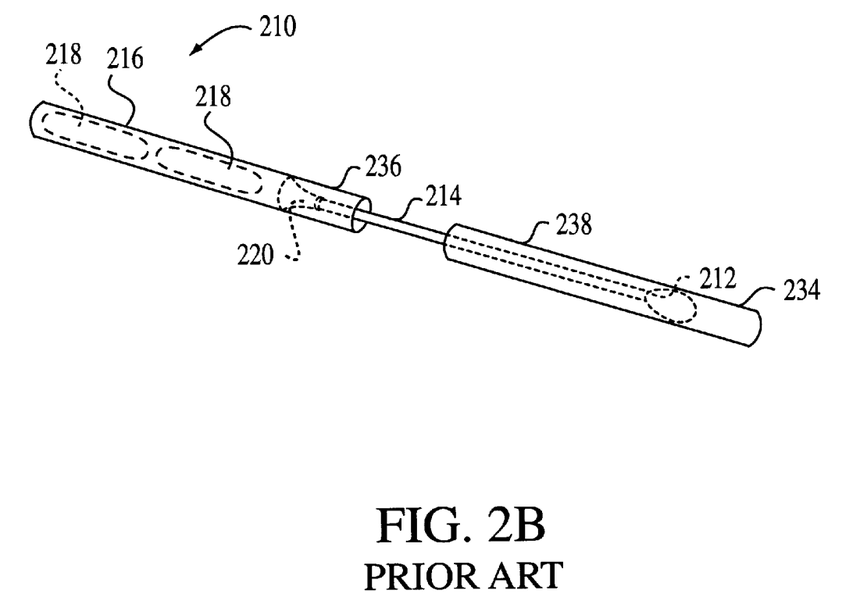

U.S. Pat. No. 4,707,450 to Nason, incorporated herein by reference, relates to a specimen collection and test device as illustrated in FIGS. 2a and 2b. This device consists of a cotton-tipped swab 214 having an elongated tubular handle 216 and a cap 234 which covers the swab and attaches to the tubular handle. The tubular handle may contain a reagent 218 which, when released, will saturate the swab tip 212. This device contains several disadvantages for forensic evidence collection. First, the device only allows for the collection and storage of a single evidence-containing swab. Second, this device requires a specially designed swab which is attached to a tubular shank rather than an ordinary cotton-tipped swab. Further, this device provides no means for identification, labeling, or sealing to prevent tampering or contamination.

Figure 3A:
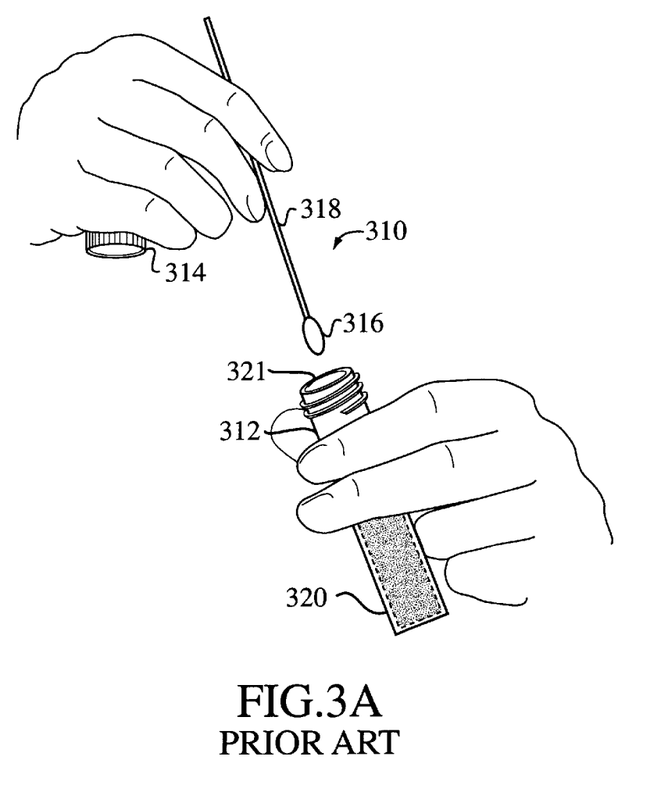
Figure 3B:
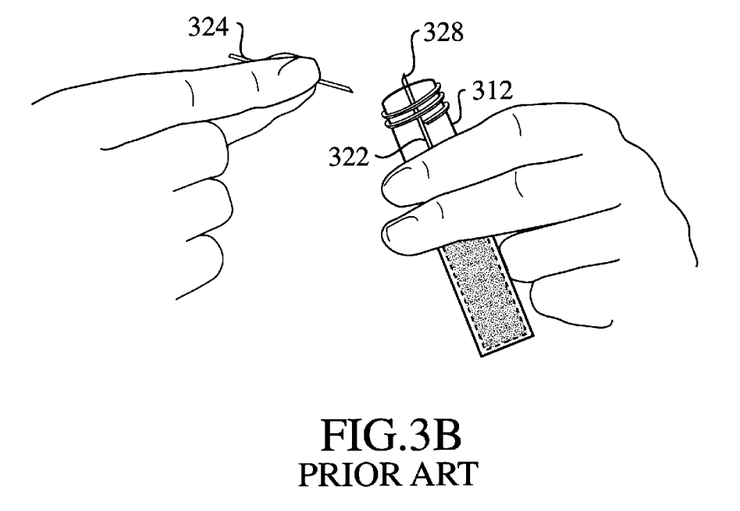
Figure 3C:
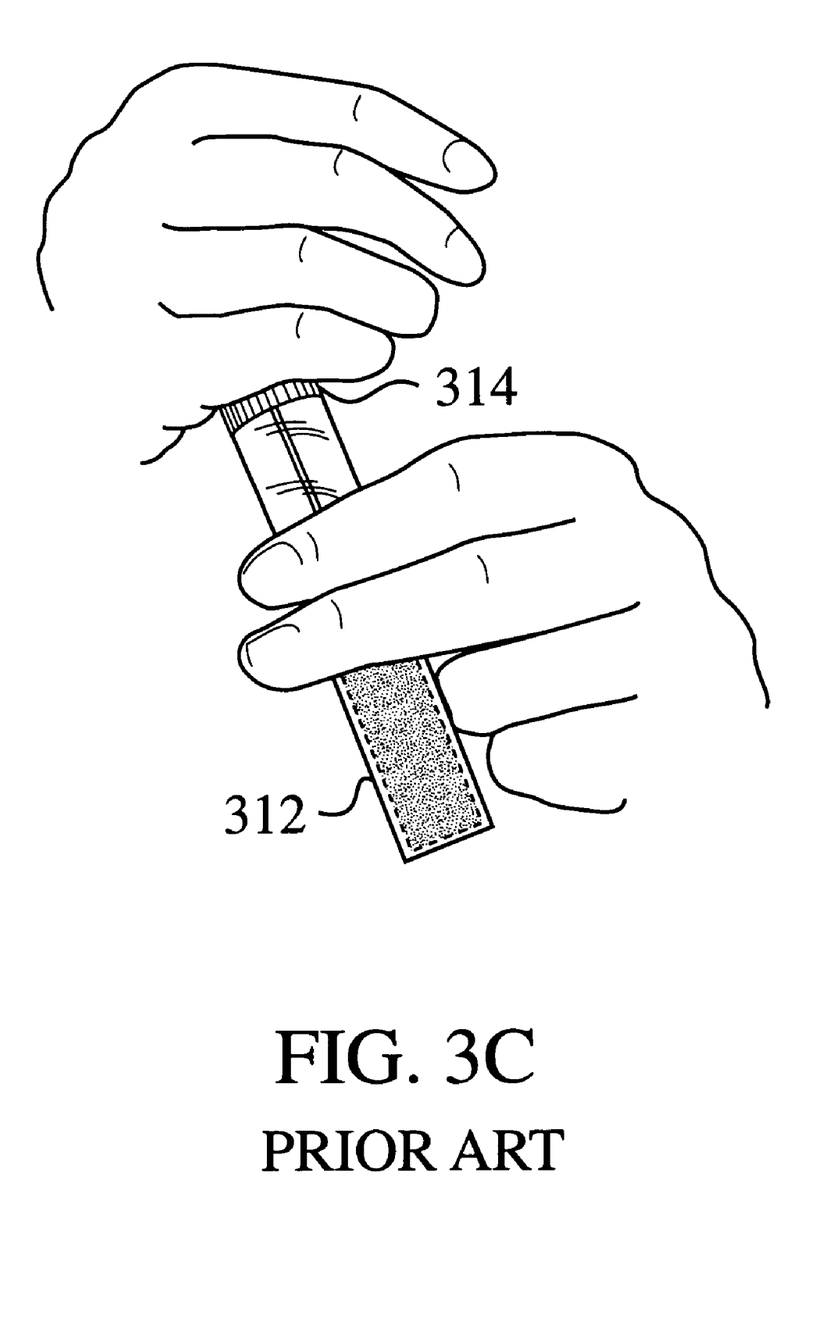

U.S. Pat. No. 4,803,998 to Kezes, et al., incorporated herein by reference, is illustrated in FIGS. 3a–3c. This patent relates to a combination of a cotton-tipped swab 310, a containment vial 312 and a cap 314. A user collects biological material using the swab and then places the swab into the vial. The user then breaks the shaft 318 of the swab at a predetermined location such that the swab matches the length of the vial as shown in FIG. 3b. The user then inserts the cap over the vial to contain the swab. This collection system contains several disadvantages. First, the system only allows for the collection and storage of a single evidence containing swab. Second, this system requires a specially-designed swab which is attached to a tubular shank rather than an ordinary cotton-tipped swab. Further, this device provides no means for identification, labeling, or sealing to prevent tampering or contamination. Further, this system also does not position the swab for contact free drying.

Figure 4:
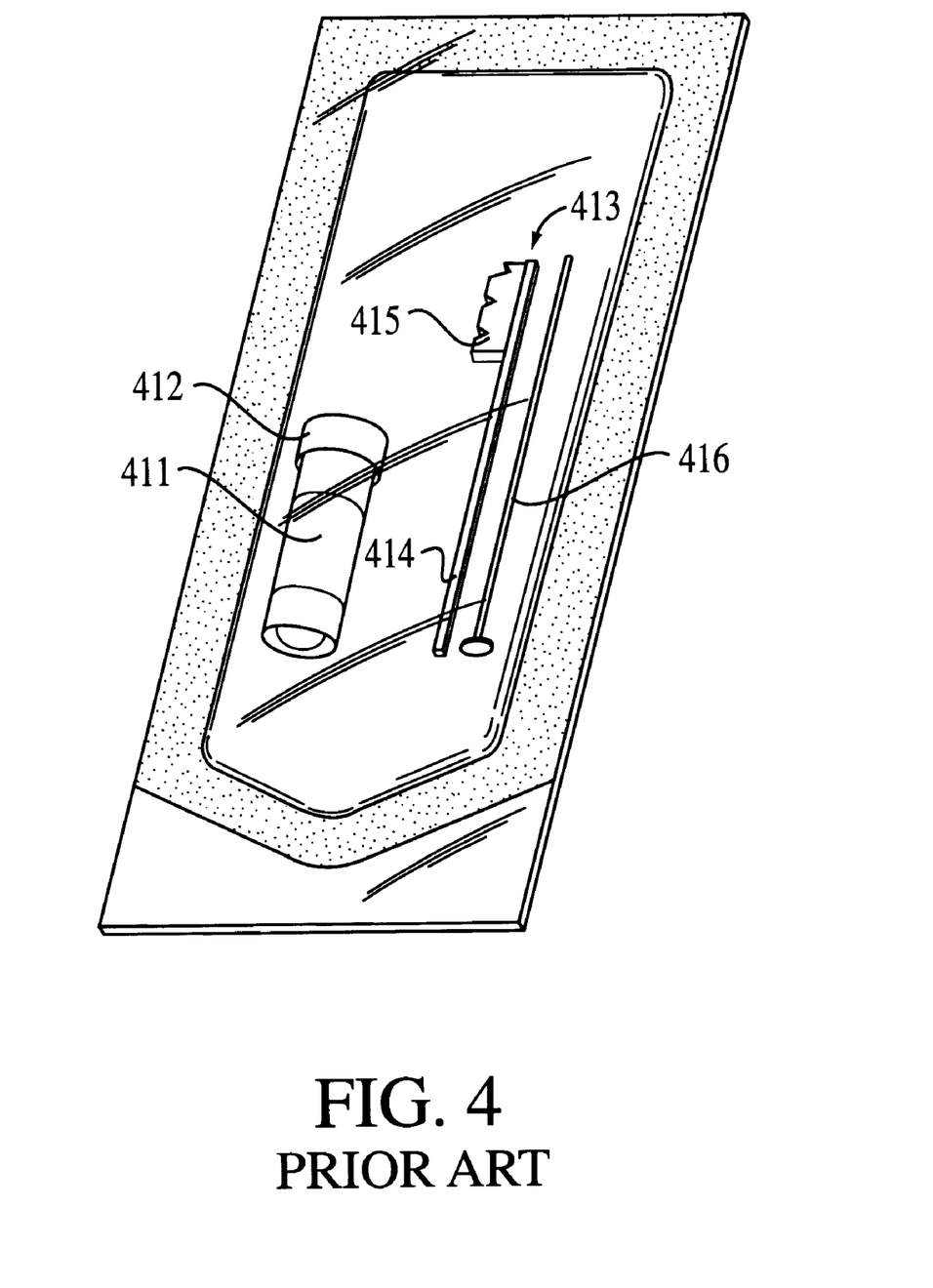

U.S. Pat. No. 5,477,863 to Grant, incorporated herein by reference, is illustrated in FIG. 4. This patent relates to a collection kit which contains a holder 414, a swab 415, a container 411 and cap 412, and a plunger 416, all of which are contained in a package 413. The user collects biological evidence on the swab and then places the swab into the container. The user then uses the plunger to break the swab from its handle. The user then seals the filled container with a cap.

This collection system also contains several disadvantages. First, the system only allows for the collection and storage of a single evidence-containing swab. Second, this system requires a specially-designed swab which is attached to a tubular shank rather than an ordinary, inexpensive, cotton-tipped swab. Further, this device provides no means for identification, labeling, or sealing to prevent tampering or contamination. Further, this system also does not position the swab for contact free drying which may lead to degradation of biological material.

Accordingly, we have determined that it is desirable to provide an inexpensive, portable apparatus for the collection and long-term storage of biological evidence, other evidence or samples requiring collection. We have also determined that it is desirable to provide a method for the collection of biological evidence or other evidence or samples which uses ordinary cotton-tipped swabs. We have also determined that it is desirable to provide an apparatus which allows for the contact-free drying of evidence-containing cotton-tipped swabs.

We have also determined that it is desirable to provide an apparatus that allows for the collection and storage of more than one evidence-containing swab. We have also determined that it is desirable to provide a device which prevents the evidence on one swab from touching the other swab. We have also determined that it is desirable to provide an apparatus that can be labeled to identify the source of the evidence, as well as its chain of possession.

In addition, we have determined that it is desirable to provide an apparatus that provides sealing of evidence to prevent tampering and contamination. Finally, we have determined that it is desirable to package an evidence collection, storage, and preservation apparatus into a kit which can be used by a single investigator or multiple investigators.

SUMMARY OF THE INVENTION

It is a feature and advantage of the present invention to provide an inexpensive, compact apparatus for the long-term storage of biological evidence, other evidence or samples requiring collection.

It is another feature and advantage of the present invention to provide for contact-free drying to prevent contamination of collected biological samples or other samples and to prevent degradation of biological samples.

It is another feature and advantage of the present invention to provide an apparatus for evidence and/or sample collection without requiring the use of reagents or other media or any pretreatment of the swabs, such as air drying before packaging or placing into a swab dryer (drying in a stream of air) before packaging.

It is another feature and advantage of the present invention to provide an apparatus which allows for the storage of multiple biological samples or other samples, while preventing the samples from contacting each other.

It is another feature and advantage of the present invention to allow investigators and subsequent handlers to identify collected evidence and record the chain of possession directly on the storage apparatus.

It is another feature and advantage of the present invention to prevent tampering of evidence through the use of seals which must be broken in order to access the evidence.

It is another feature and advantage of the present invention to package an evidence collection, storage, and preservation apparatus into a kit which can be used by a single investigator or multiple investigators.

The present invention is based, in part, on our recognition of the benefits of providing forensic investigators with an apparatus for contact-free drying, storage, and identification of biological evidence or other samples. The goals of the present invention are to improve the protection and preservation and biological evidence in a labeled and sealed safe environment.

To achieve the above features and advantages, a box includes a receiving section which is used to hold cotton-tipped swabs. An investigator collects evidence on the swabs, places the swabs into the receiving section, and closes the box. The investigator then seals the box to prevent tampering and labels the box to identify the evidence and/or its chain of possession.

In the preferred embodiment of the present invention, the box consists of a single piece of foldable cardboard. The cardboard is creased and adapted with a receiving section such that, when folded along the creases, the cardboard forms a box and the receiving section holds swabs inside of the box. The box may be provided as part of a kit which includes one or more boxes, one or more swabs, one or more containers of sterile solution to moisten the swabs, seals, labels, and a sterile package. The box may house a single swab, two swabs or multiple swabs.

In addition, the box may be comprised of multiple pieces of cardboard, plastic, metal or the like. That is, any material which provides the functions of the box described herein, in any combination of sections or pieces may be used. The receiving sections may be perforated and/or integral with the box. Alternatively, the receiving sections may simply be affixed to the inside of the box. The receiving sections may include a hole for receiving the swabs, or other configuration such as a slot, indentation, hook, and the like, to secure the swab to the interior of the box. The box preferably holds the swabs in the interior without touching the inner walls for contact free drying. However, contact free drying is an optional feature.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

The scope of the invention, together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter which illustrate preferred embodiments of the invention.

DESCRIPTION OF THE PREFERRED EMBODIMENT OF THE INVENTION

The present invention is an apparatus for the collection, drying, storage, identification, and protection of biological evidence or other evidence/samples. The evidence may be collected on one or more cotton-tipped swabs. The swabs are then stored inside a sealed, labeled box in a manner such that the cotton tips of the swabs are prevented from contacting either the box or each other.

Figure 5:
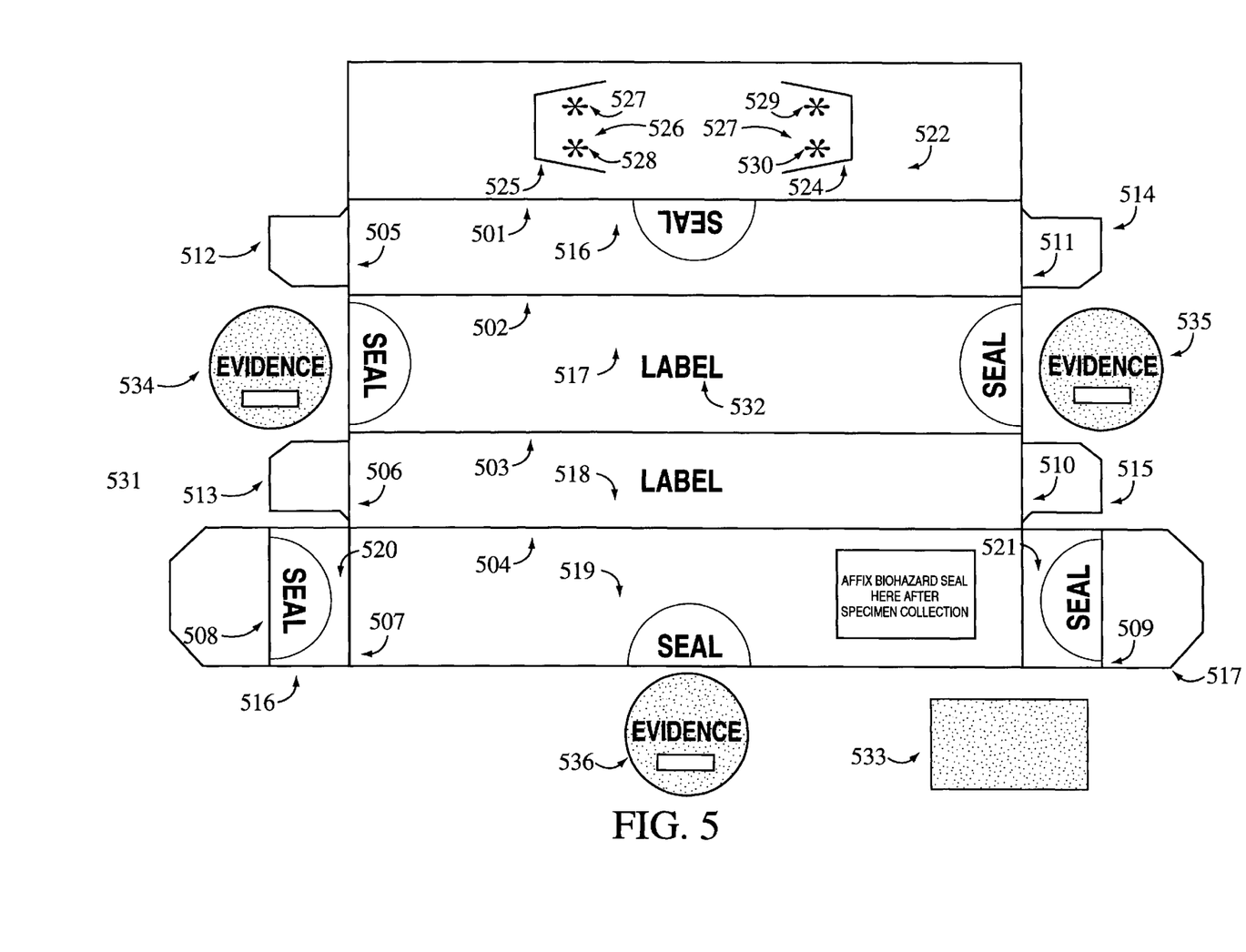
FIG. 5 depicts the design of the foldable cardboard box and the approximate location of labels and seals.

FIG. 5 illustrates how a single piece of corrugated cardboard may be designed such that it will form a box suitable for the storage of evidence. Four inner end flaps 512–515 and two outer end flaps 516–517 are integral with the cardboard. The cardboard is pre-folded with four inner creases 501–504 and eight outer creases 505–511 such that, when folded along the inner and outer creases, the cardboard forms a box having four side panels 516–519, two end panels 520–521, and an inner panel 522. The inner panel is perforated with two seams such that two flaps or receiving sections 524–525 are formed when pressure is applied to break the seams. Alternately, the flaps may be formed of separate pieces of cardboard and affixed to the inner panel via glue, staples or other suitable connection means. The flaps may be of any suitable configuration or shape. The flaps contain star-shaped perforations 527–530 which are sized and positioned such that a cotton-tipped swab will slide into each of the flaps through the star-shaped perforations.

While the cotton swabs are depicted in FIG. 1 having a specific configuration and tip of cotton, other type of swabs may also be used with different configurations, such as a swab with two cotton tips, and/or different absorbent materials on the tip.

The perforations 527–530 may be of any suitable shape, other than star-shaped. In addition, the flaps need not be perforated as merely a hole, but may be slotted with one or more suitable slots or fitted with hooks or other devices that perform similar functions as the different shaped perforations. In this configuration, the slots may optionally include a well-shaped or circular shaped hole at the end of the slot to facilitate insertion of the swab or other evidence collection member. This slot-like configuration facilitates or makes possible the use of a swab with absorbent materials on both ends, thereby increasing the amount of evidence that may be collected therein, since the double-ended swab may be pushed into the slots on either end for securing to the box.

In addition, while the flaps have been depicted as being of a flat configuration with holes or slots for securing the swab, the flaps may alternatively be bendable, forming a substantially flat surface for placement of the swabs or other collection device thereon. In this configuration, the swab may be secured to the flaps without the need of a hole or slot therein, but with the use of a predeposited adhesive or securing tape. In addition, this configuration facilitates various shaped swabs or collection devices to be secured in the interior of the box, while providing the ability for contact-free drying and/or preventing contamination of the sample contained therein.

Further, while the flaps have been depicted as requiring pairs of flaps to secure the collection devices/swabs to the interior of the box, a single flap may be sufficient for this purpose as well, for example, where the absorbent material end of the swab is angled upward and is secured or inserted close to the flap. Of course, more than two flaps may also be used.

One or more evidence collection labels 531–532 and biohazard labels 133 may be affixed to or integral with the box to describe the source and type of evidence, to identify the chain of custody of the evidence, and to identify the potential biological hazards associated with contacting the evidence. After the box is closed, at least three seals 533–535 are preferably affixed to the side panels and end flaps of the box to prevent tampering of the evidence. Of course, seals are an optional feature of the present invention.

Figure 6:
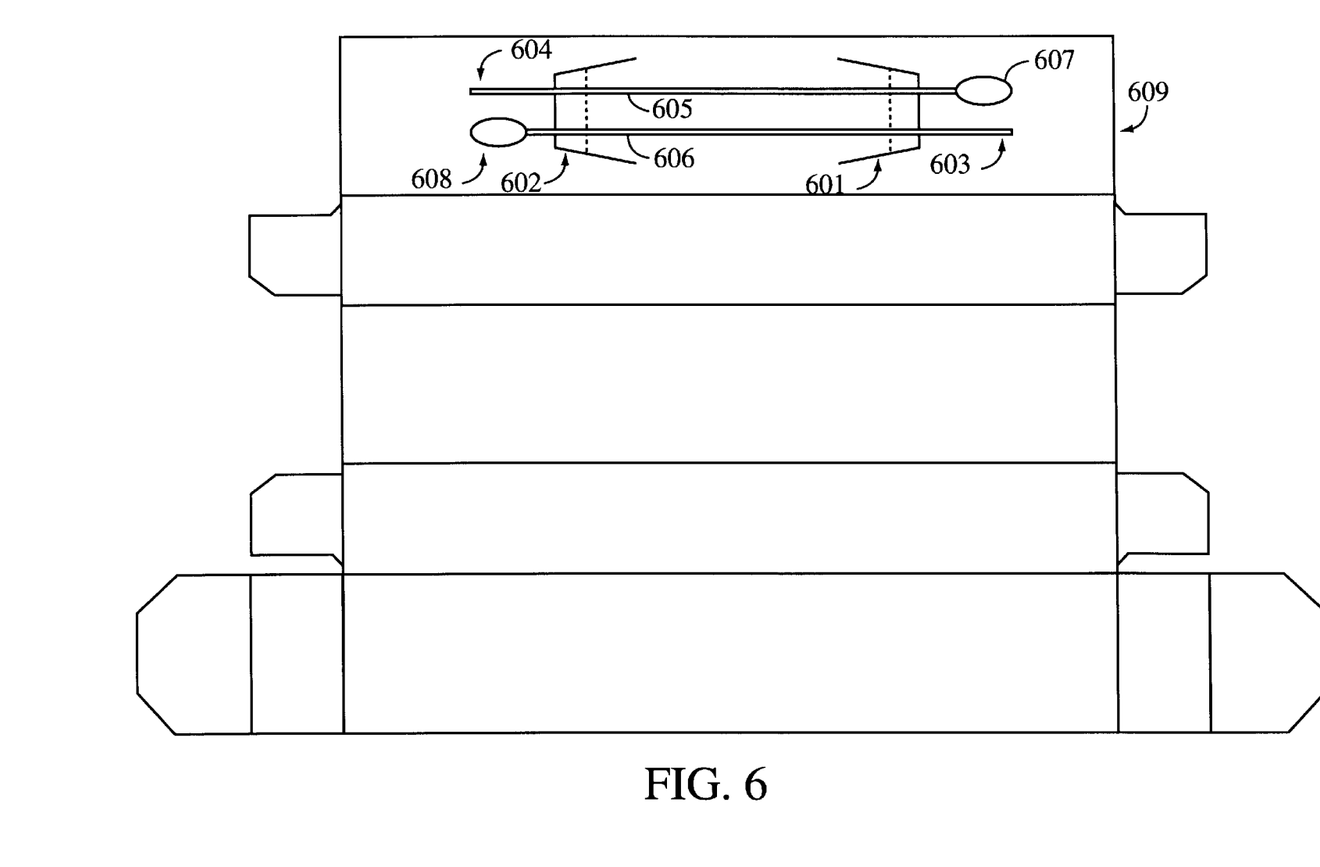
FIG. 6 depicts the inside of the foldable cardboard box (smaller version) and illustrates how cotton-tipped swabs are held in the receiving section of the box.

FIG. 6 depicts the inside view of the foldable cardboard box and illustrates how the cotton-tipped swabs 605–606 may be held in the inner panel receiving section 609 of the box. The cotton-tipped swabs 603–604 are placed into the receiving section such that the shaft of each swab 605–606 passes through the flaps 601–602. The swabs may be optionally placed in the receiving section such that the cotton tips 607–608 are opposite each other to prevent biological evidence from dripping onto one cotton tip from the other cotton tip.

Figure 7:
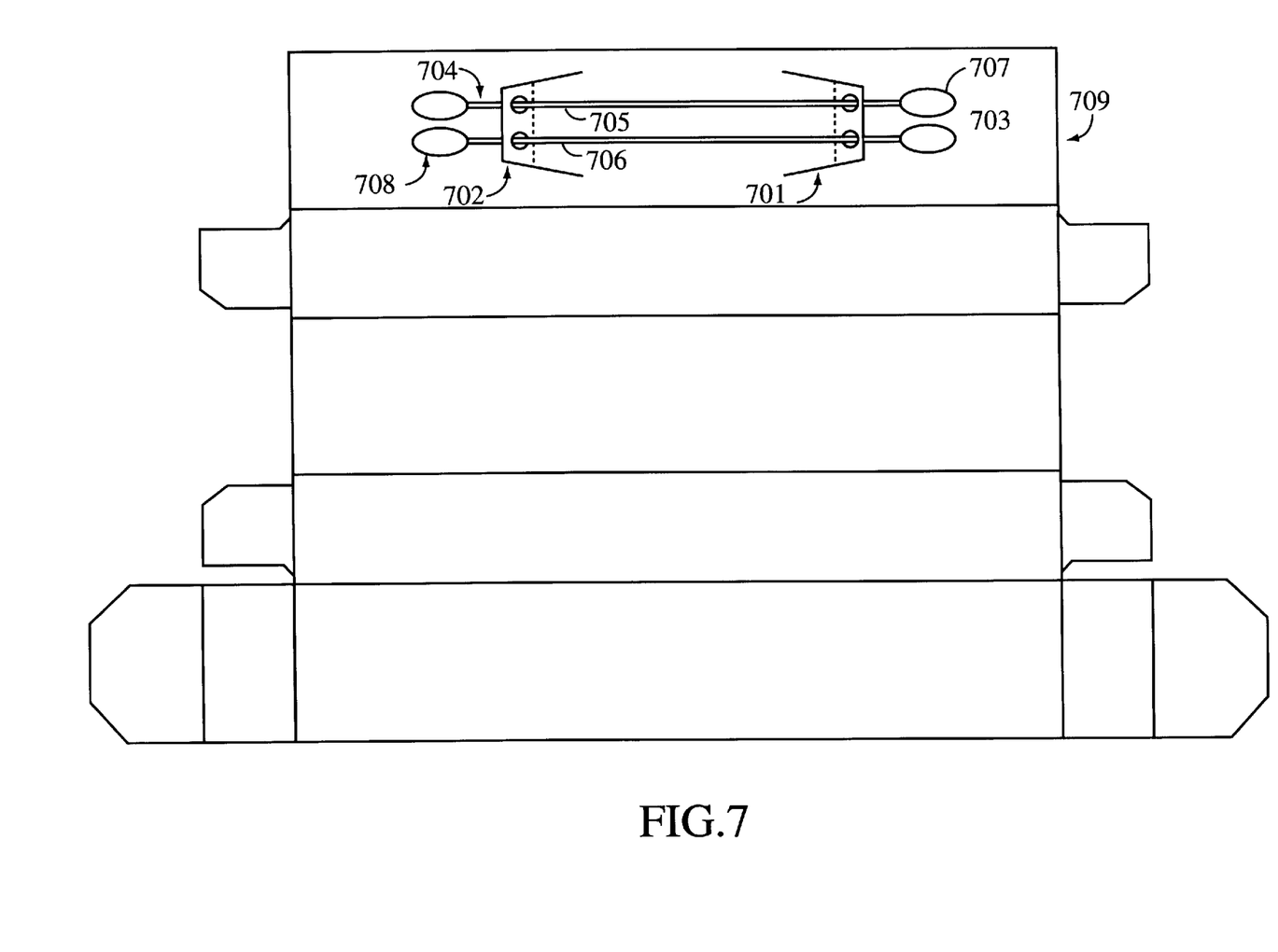
FIG. 7 illustrates how different types of swabs may be used in the foldable cardboard box.

FIG. 7 depicts an inside view of the foldable cardboard box and illustrates how other types of swabs, such as swabs with two cotton tips, may be used.

Figure 8A:
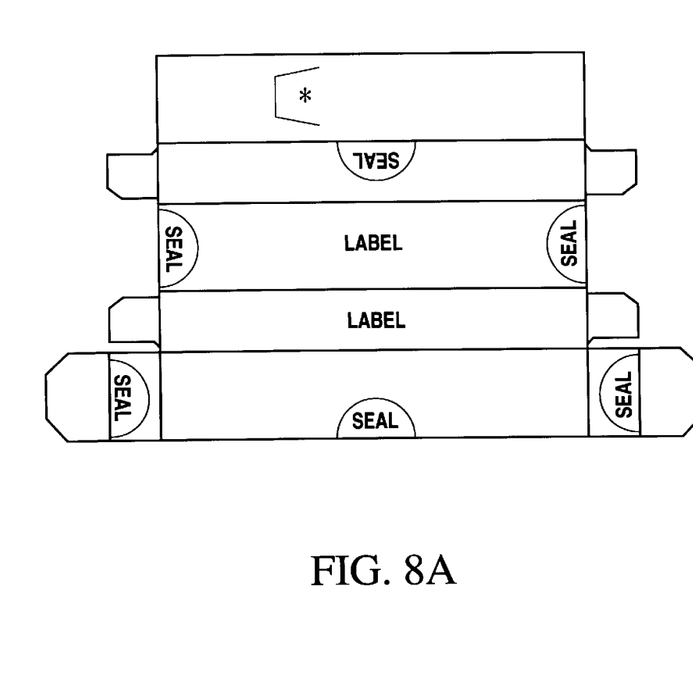
FIGS. 8a and 8b depict foldable cardboard boxes having alternate types of receiving sections.
Figure 8B:
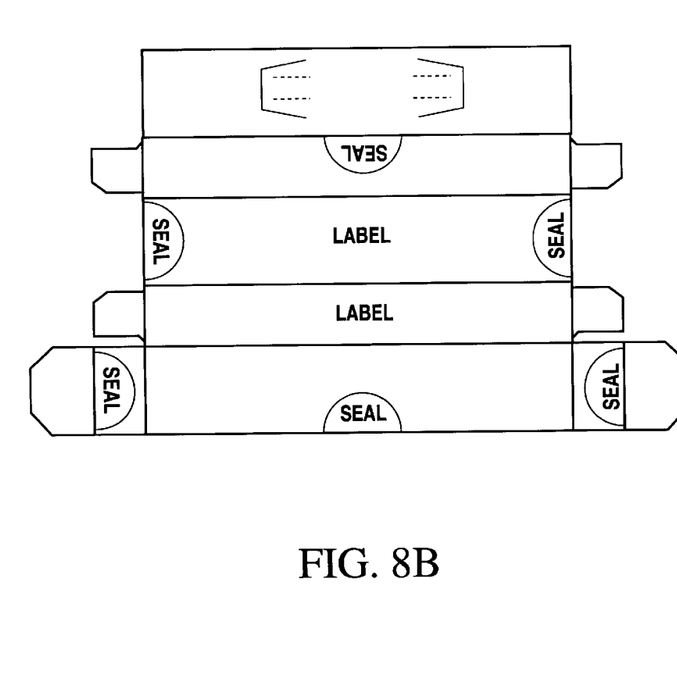

FIG. 8a–8b depicts various alternate receiving sections. FIG. 8a depicts a receiving section with a single flap such that the cotton tips of the swabs remain contact-free while the shaft of each swab may contact the box. FIG. 8b depicts a receiving section which has slots instead of holes.

Figure 9:
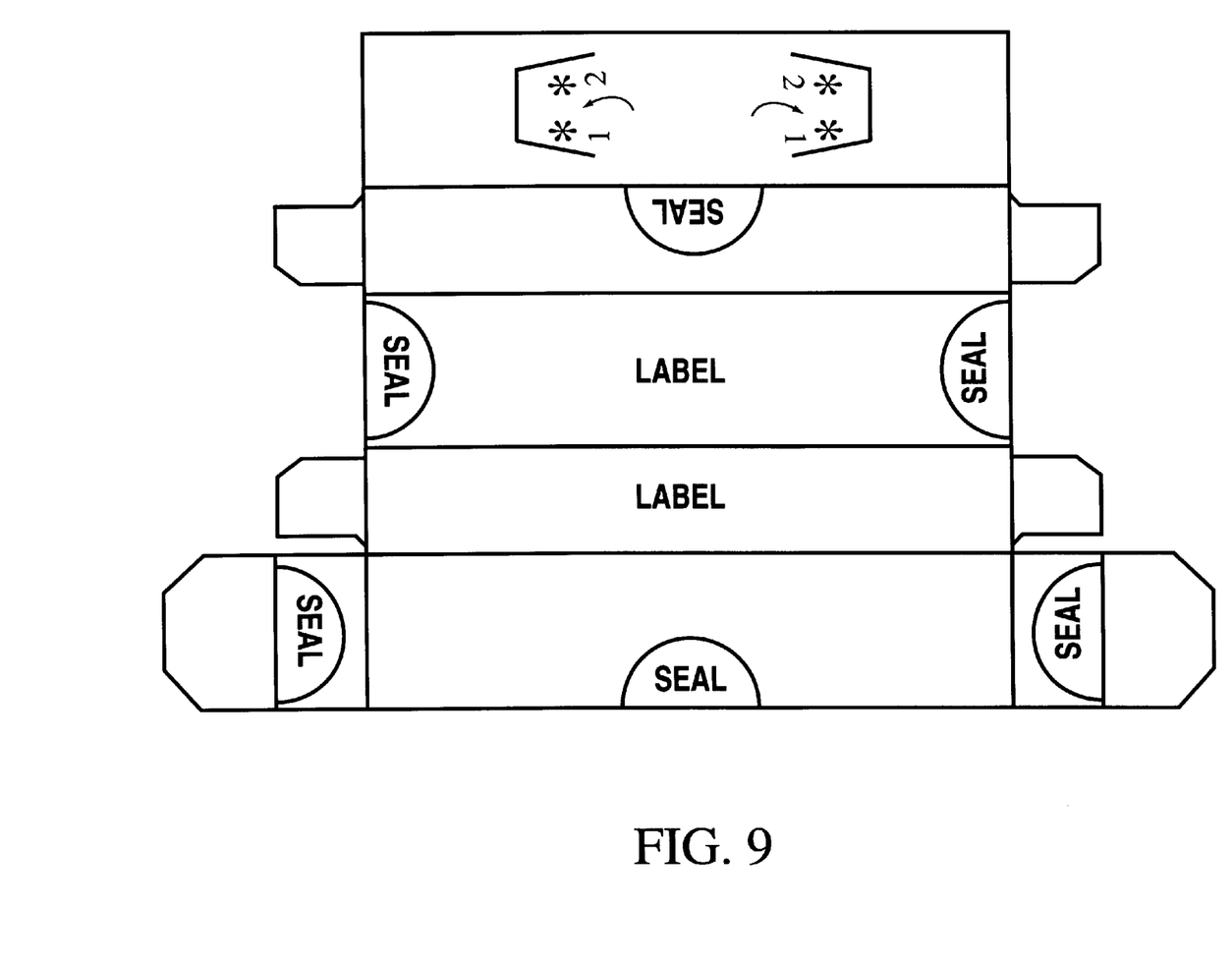
FIG. 9 depicts a smaller version of the foldable cardboard box, thus illustrating that the size of the box may vary.

FIG. 9 depicts a smaller version of the box of FIG. 5, thus illustrating that the present invention may vary in size so long as it is large enough to contain the cotton-tipped swabs or other shaped collection device that are used to collect biological evidence. The user may break the shaft of the swab(s) such that the swab(s) matches the length of the box.

Figure 10:
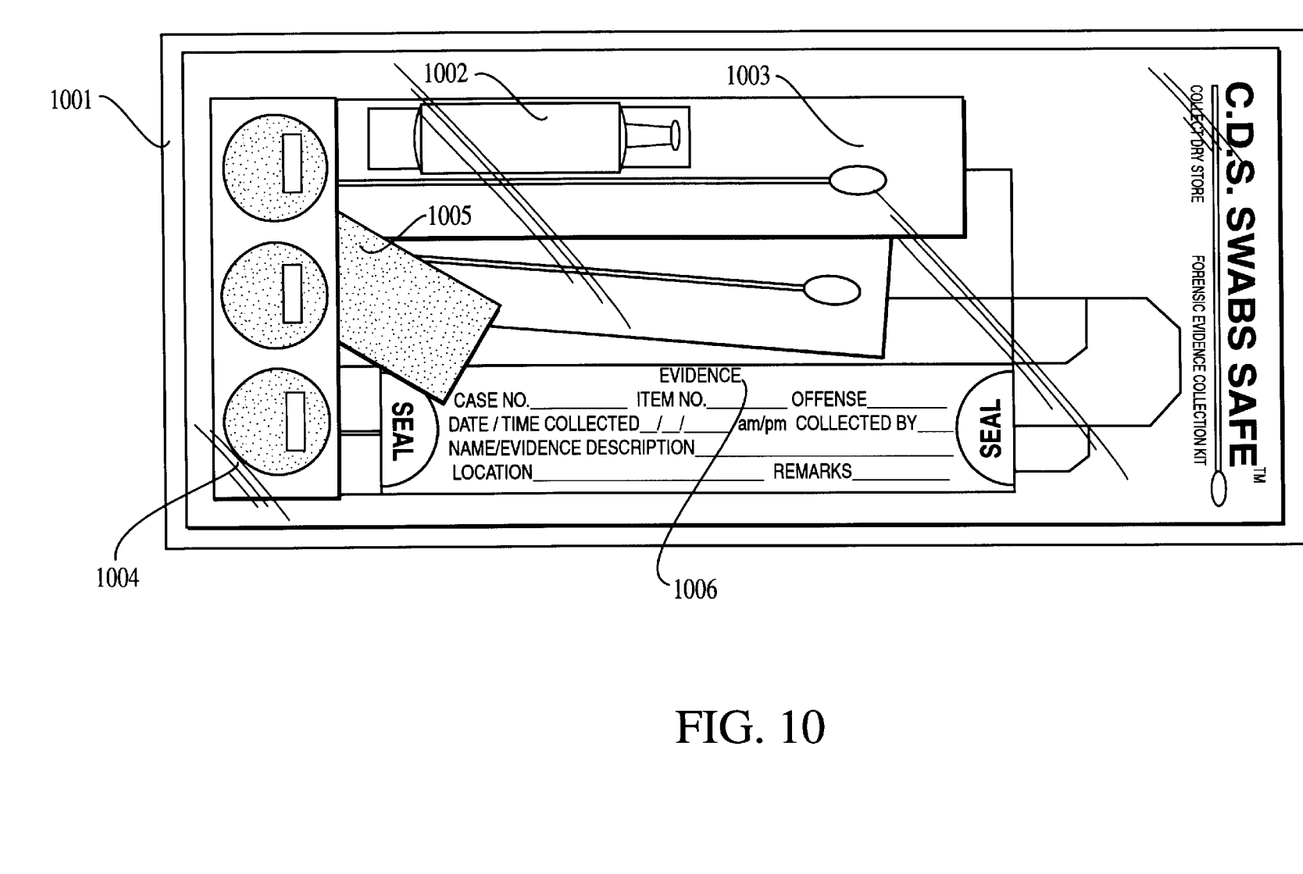
FIG. 10 depicts an evidence collection kit comprising sterile packaging, one or more foldable cardboard boxes, one or more sterile solution dispensers, a plurality of sterile or unsterile cotton-tipped swabs, at least three evidence seals to prevent tampering, one or more biohazard labels, and one or more identification labels.

FIG. 10 illustrates how the present invention may be packaged into a kit which can be used by a single investigator or multiple investigations for the collection of evidence. The kit includes one or more dispensers of optionally sterile solution 1002, two or more absorbent material and optionally sterile swabs, such as a cotton-tipped swab 1003, at least, for example, three evidence seals 1004, one or more biohazard labels 1005, and one or more foldable cardboard evidence storage boxes with one or more integral evidence identification labels 1006. All of the above items are contained preferably in a packaging 1001, which may be optionally sterile.

Figure 11:
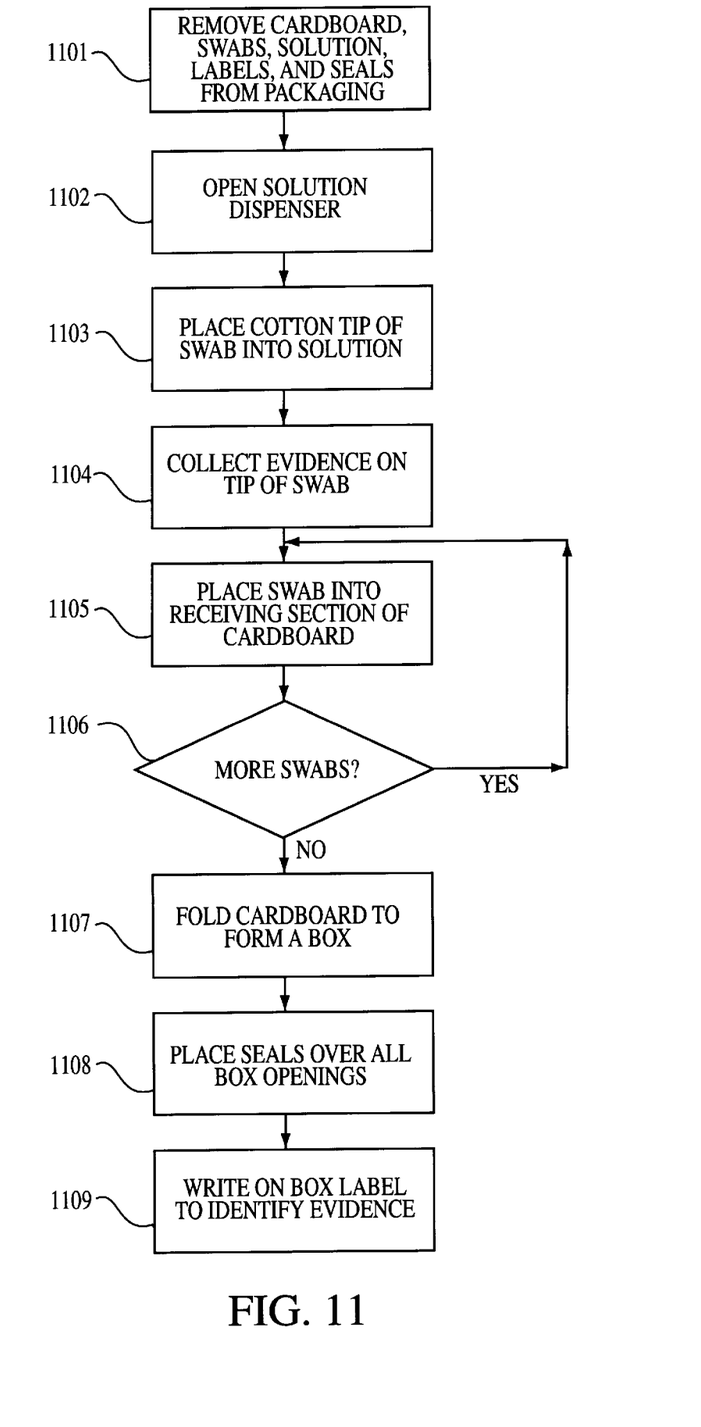
FIG. 11 is a flowchart of the process by which an investigator may collect biological evidence using the present invention.

FIG. 11 is a chart depicting an exemplary process by which an investigator may use the kit depicted in FIG. 10 to collect, identify, and store evidence. In step 1101, the investigator opens the packaging and removes a foldable cardboard box, the cotton-tipped swabs, a solution dispenser, and the labels and seals that are contained inside. In step 1102, the investigator opens the solution dispenser, and the investigator optionally moistens the cotton tip of a swab by placing solution onto the tip of a swab in step 1103.

In step 1104, the investigator then collects evidence with the moistened swab. As an alternative, depending on the nature of the evidence, the investigator may collect the evidence on the tip of a dry swab. This applies if liquids or body fluids are collected. In step 1105, the investigator places the swab into the receiving section of inner panel of the box. If additional swabs are available, the investigator may repeat steps 1103 through 1105. When all swabs are used as determined in step 1106, the investigator folds the cardboard along the creases to form a box in step 1107. In step 1108, the investigator places seals over preferably all box openings. Finally, the investigator labels the box and writes on the box to identify the evidence in step 1109.

Figure 12A:
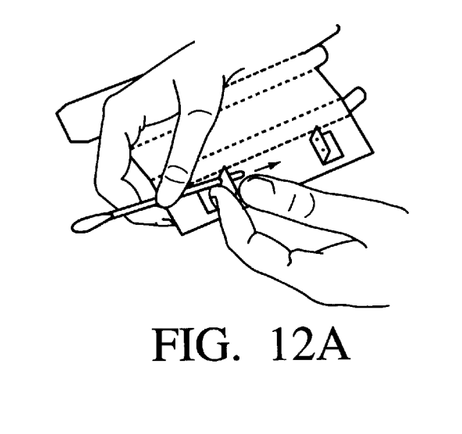
FIGS. 12a–12d illustrate the steps of the process by which an investigator may: (1) place swabs containing collected evidence into the receiving section of the foldable cardboard box; (2) fold the cardboard to form a box; (3) seal the box to prevent tampering; and (4) label the box to identify the evidence and chain of possession.
Figure 12B:
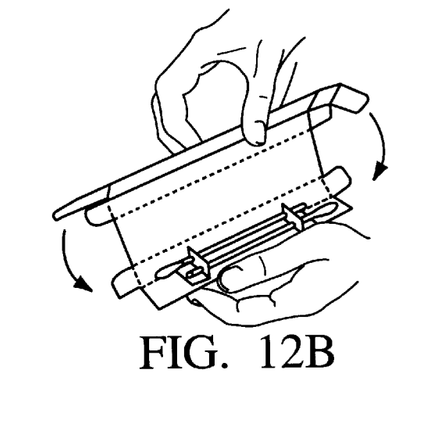
Figure 12C:
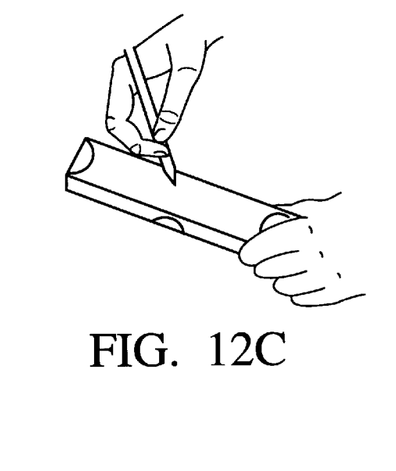
Figure 12D:
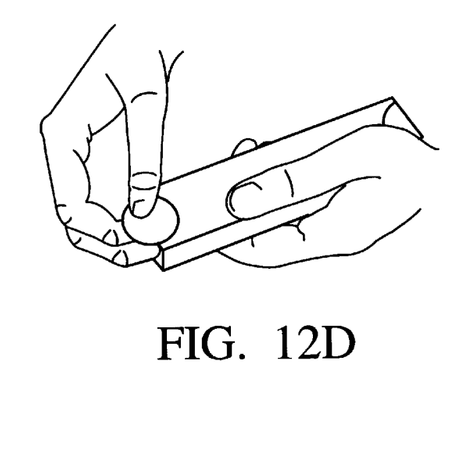

FIGS. 12*a*–12*d* illustrate how the investigator performs several of the steps described above using the foldable cardboard box. FIG. 12*a* depicts how the investigator inserts a swab into receiving section (i.e., the perforations that are on the flaps of the inner panel) of the box. FIG. 12*b* depicts how, after inserting evidence-containing swabs into the receiving section, the investigator folds the cardboard along the creases to form a box. FIG. 12*c* depicts how the investigator places seals over the openings of the box to prevent tampering. Finally, FIG. 12*d* depicts how the investigator may write on the label of the box to identify the evidence and its chain of custody.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An apparatus for collecting and storing collection samples including biological evidence, comprising:
    (a) at least one evidence collection devices, each of said evidence collection devices comprising:
        (i) a shaft having two ends; and
        (ii) a material which is attached to one shaft end in a pattern to form a swab; and
    (b) at least one box comprising a unitary piece of material, said box having an inside, an outside, and at least one opening locations;
    (c) at least one receiving section sized and positioned such that said receiving section is at least one of integral with and attached to the inside of the at least one box and is adapted to receive the at least one evidence collection devices, such that the swab remains contact free;
    (d) at least one label, said label comprising:
        (i) a paper strip having two sides; and
        (ii) an adhesive material affixed to one side of the paper strip such that the paper strip will adhere to the outside of the at least one box; and
    (e) a plurality of seals, said seals having two sides and an adhesive material affixed to one side such that the seals will adhere to the opening locations of the at least one box.

2. The apparatus for collecting and storing biological evidence according to claim 1, further comprising:
    (a) sterile solution; and
    (b) at least one container to hold the sterile solution for moistening the evidence collection devices.

3. The apparatus for collecting and storing biological evidence according to claim 2, further comprising packaging sized to hold the at least one box, the at least one evidence collection devices, the at least one label, the plurality of seals, and the at least one container.

4. An apparatus for collecting and storing biological evidence, comprising:
    (a) at least one evidence collection devices, each of said evidence collection devices comprising:
        (i) a shaft having two ends; and
        (ii) cotton material which is attached to one shaft end in a bulbous pattern to form a swab; and
    (b) at least one box comprising a unitary piece of material, said box having an inside, an outside, and one or more opening locations;
    (c) a receiving section sized and positioned such that said receiving section is attached to the inside of the at least one box and is adapted to receive the at least one evidence collection devices, such that the swab remains contact free;
    (d) at least one label, said at least one label being one of integral to and attachable to the outside of the at least one box; and
    (e) a plurality of seals, said seals having two sides and an adhesive material affixed to one side such that the seals will adhere to the opening locations of the at least one box.

5. The apparatus for collecting and storing biological evidence according to claim 4, further comprising:
    (a) a sterile solution; and
    (b) at least one container to hold the sterile solution for moistening the evidence collection devices.

6. The apparatus for collecting and storing biological evidence according to claim 5, further comprising packaging sized to hold the at least one box, the at least one evidence collection devices, the at least one label, the plurality of seals, and the at least one container.

* * * * *